United States Patent [19]

Imboden et al.

[11] 4,240,160
[45] Dec. 23, 1980

[54] CUT AND SEWN SURGICAL STOCKINGS

[75] Inventors: Walter H. Imboden, Burlington, N.C.; David M. Lieberman, New York, N.Y.

[73] Assignees: Burlington Industries Inc., Greensboro, N.C.; by said Walter H. Imboden; Hoffmann-La Roche Inc., Nutley, N.J.

[21] Appl. No.: 972,717

[22] Filed: Dec. 26, 1978

[51] Int. Cl.$^2$ ............................................. A41B 11/00
[52] U.S. Cl. .................................. 2/239; 66/178 A; 112/262.2
[58] Field of Search ............... 2/239; 66/178 A, 190, 66/192, 193, 195; 112/262.2; 128/160, 165, 157, 155, 156, 555, 539, 445

[56] References Cited

U.S. PATENT DOCUMENTS

| | | | |
|---|---|---|---|
| 471,349 | 3/1892 | Cooper | 66/192 |
| 707,659 | 8/1902 | Ware et al. | 2/239 X |
| 1,954,711 | 4/1934 | Oliver et al. | 66/192 |
| 1,984,326 | 12/1934 | Titone | 66/176 |
| 2,010,787 | 8/1935 | Mendez | 66/195 X |
| 2,019,183 | 10/1935 | Herberlein | 57/292 |
| 2,019,185 | 10/1935 | Kagi | 57/247 |
| 2,150,133 | 3/1939 | Seidel | 66/172 E |
| 2,334,206 | 11/1943 | Knohl | 66/187 |
| 2,445,049 | 7/1948 | Welch | 2/239 |
| 2,485,004 | 10/1949 | Leuliette | 2/239 |
| 2,564,245 | 8/1951 | Billion | 66/202 X |
| 2,574,873 | 11/1951 | Jobst | 128/165 |
| 2,691,221 | 10/1954 | Jobst | 128/155 X |
| 2,768,385 | 10/1956 | Gordon | 66/178 R X |
| 2,948,132 | 8/1960 | Gift | 66/178 |
| 3,077,758 | 2/1963 | Siciliano | 66/192 |
| 3,301,018 | 1/1967 | Knohl | 66/202 |
| 3,552,154 | 1/1971 | Lesley | 66/192 |
| 3,552,155 | 1/1971 | Hartung | 66/192 |
| 3,910,075 | 10/1975 | Holiday | 66/192 |
| 4,086,790 | 5/1978 | Hanrahan et al. | 66/178 |

Primary Examiner—Ronald Feldbaum
Attorney, Agent, or Firm—Cushman, Darby & Cushman; Jon S. Saxe; George M. Gould

[57] ABSTRACT

A method of manufacturing support garments for human extremities, and the garments so produced. A support garment form is cut from a sheet of warp-knit power fabric, the fabric having a lengthwise (machine) dimension of greatest stretch and power, and a filling dimension (the cross-machine direction) in which the stretch is incidental (i.e., about 250%/80% or at least 2/1) and the sheet being orientated during cutting so that the lengthwise dimension of the sheet extends circumferentially in the final garment produced. The edges of the garment formed are seamed to produce the final support garment, the seam extending along the dimension of elongation of the extremity on which the support garment fits. The garment is preferably dimensioned so that the compression provided by the garment is greatest at the portion of the garment disposed most remote from the human torso along the human extremity on which it is disposed, the compression continuously gradually decreasing from the most remote portion of the extremity toward the torso. Tricot and raschel warp-knit power fabrics are preferred.

17 Claims, 4 Drawing Figures

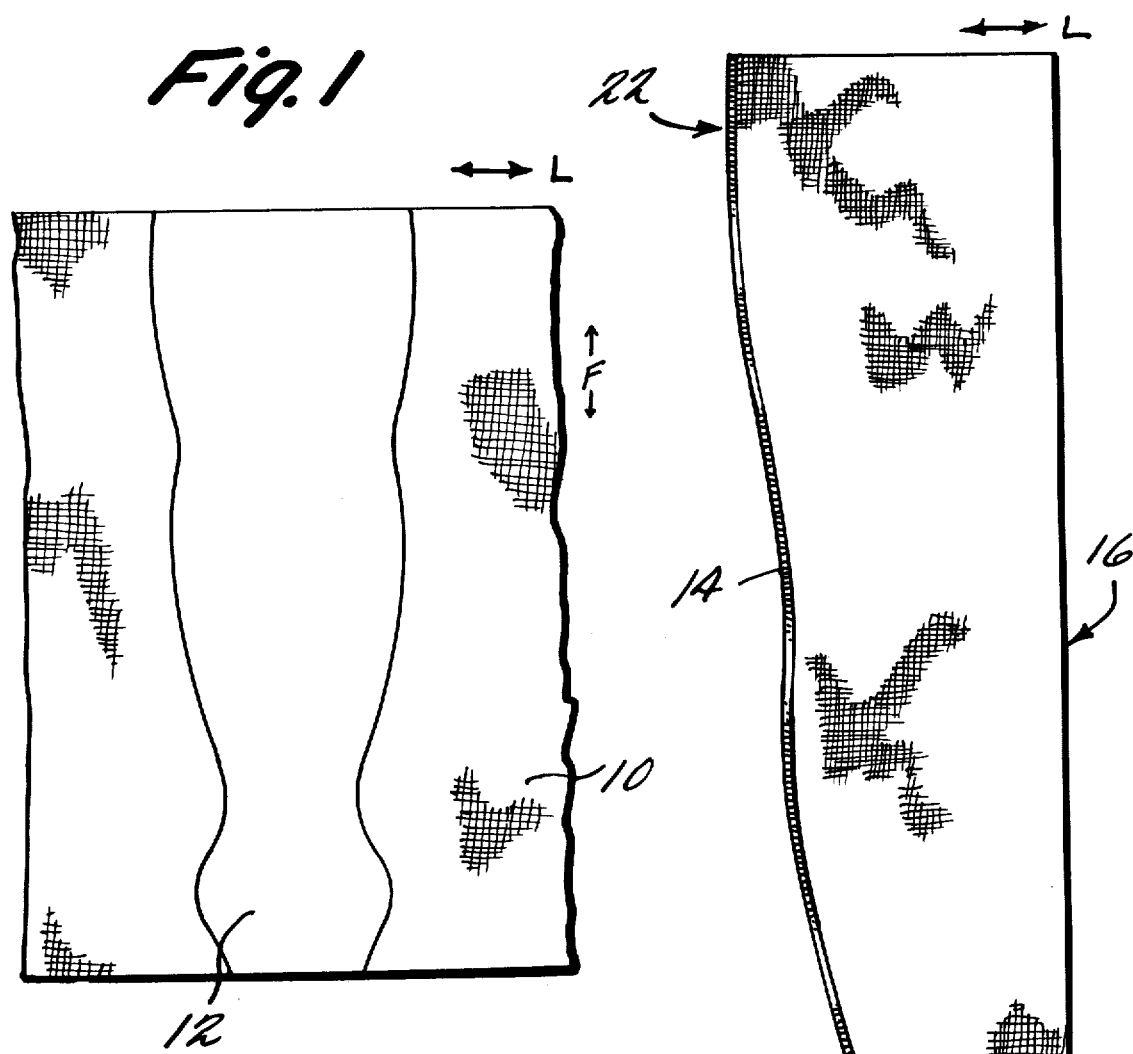

CUT AND SEWN SURGICAL STOCKINGS

BACKGROUND AND SUMMARY OF THE INVENTION

A variety of support garments are on the market today. The purpose of support garments is to overcome the elevated internal pressures within a human extremity caused by gravity or disease processes. In many individuals the venous valves which normalize the pressure in the veins of a vertically oriented extremity are inherently too few in number, incompetent, damaged, diseased or otherwise poorly functional. In such cases blood must be returned to the heart from the extremities in long, unsegmented columns in which the pressure exceeds the normal pressure for that level and may result in swelling, stasis ulcers, varicose veins, and other vascular and dermatological diseases. Support garments are designed to provide sufficient external circumferential counter pressure to maintain the normal venous and lymphatic pressures at a given leval in the extremity, thus assisting the movement of venous blood and lymphy from the extremity.

There are numerous problems associated with prior art support garments. Commercial prior art support garments are often circular knit (see U.S. Pat. No. 4,086,790); due to limitations in the tubular fabric circumferences a achievable on circular knitting machines, it is impossible to obtain the exact proportional circumferential counter pressures necessary in support stockings and other garments. In order for the support garment to be effective, the counter pressure exerted by the garment preferably must decrease more or less at a predetermined rate from the position of the extremity most distal from the torso and decreasing proximally toward the torso. There have been proposals to place inserts in such circular knit fabrics to relieve the pressures relatively adjacent to the torso; however, even such proposals do not result in a support garment having the maximum desirable counter pressures at that level.

According to the present invention, the problems inherent in prior art support garments are overcome in a simple and easy manner; according to the invention it is possible to produce support garments that have essentially the pressure gradiations characteristics that are desirable for support garments, yet such garments can be produced comparatively inexpensively according to the invention.

In general, the invention provides the manufacture of support garments utilizing cut and sew techniques with warp-knit power fabrics. The prior art is replete with suggestions for formation of stockings in general utilizing cut and sew techniques; however, heretofore such stockings have either (1) not been produced for the purpose of imparting measurable compression, or (2) have not been entirely successful in providing the necessary degree of predictability of the compression due to the presence of an excessive amount of stretch in the longitudinal (as opposed to circumferential) dimension of the garment. With respect to class (1), attention is directed to U.S. Pat. Nos. 2,768,385 and 2,445,049. In these disclosures, the fabric is knit with some stretchable yarn before the cut and sew techniques are practiced; however, the stretchable yarn is not a power yarn, and its only purpose is to oppose the tendency to bag, rather than imparting measurable compression. With respect to class (2), attention is directed to U.S. Pat. No. 2,574,873. Products are produced commercially following the teachings of that patent, utilizing an open power knit fabric having significant stretch and compression in both the longitudinal and circumferential dimensions (the warp and filling directions as originally produced), as being important and necessary. While such products are useful for their intended purposes, it has been found according to the present invention that the substantial longitudinal stretch inherent in such products can change the pre-engineered lateral compressive properties that are desired, with consequent less than perfect functioning of the products.

The method according to the present invention is for the manufacture of support garments for elongated human extremities comprising the steps of providing a sheet of warp-knit power fabric, the fabric having a lengthwise (warp) dimension of greatest stretch and power and a filling dimension in which the stretch is incidental; cutting out of the sheet a support garment form, the sheet being orientated during cutting so that the lengthwise dimension of the sheet extends circumferentially in the final garment produced and so that the filling dimension of the sheet extends longitudinally in the final garment produced; and seaming the edges of the garment formed to produce the final support garment, the seam extending along the dimension of elongation of the extremity on which the support garment is adapted to fit. The "lengthwise" dimension of the warp-knit power fabric is the direction in which during knitting the fabric exits the machine, and the direction in which spandex strands are laid. Such fabrics have a great deal of stretch and power in that direction, and much less in the "width" or cross-machine direction. Preferred warp-knit power fabrics are tricots and raschels having, for example, approximately a 250% warp stretch and only approximately an 80% filling stretch [typical of one-way stretch fabrics]; as opposed to prior art open power net constructions (as in U.S. Pat. No. 2,274,873) having about 200–220% warp or machine direction stretch, and purposefully engineered so as to have about 175–190% filling or cross-machine stretch, or prior art bag-free stockings (as in U.S. Pat. Nos. 2,445,049 and 2,768,385) having little or no compression capability. A fabric stretch of at least about twice as great in the lengthwise (warp) dimension as in the filling dimension is desired. The power yarn is utilized for the purpose of imparting measurable compression and may comprise spandex or rubber or other yarns with the distention properties of spandex. The secondary yearn or yarns which comprise the fabric can be any fiber that is capable of being warp-knit and is compatible with spandex, examples of which are nylon and polyester. According to the present method, the cutting step is practiced so that the compression provided by the garment is greatest at the portion thereof adapted to be most distal from the torso along the human extremity on which it is adapted to be disposed, and the compression accurately and predictably gradually continuously decreases proximally along the extremity toward the torso.

According to the present invention a support garment for an elongated human extremity is provided. The garment comprises a tube of warp-knit power fabric having a dimension (circumferential) in which the greatest stretch and power is provided and a dimension (lengthwise) in which the stretch is incidental (i.e., about 65–80%), the circumference of this tube varying as required so that it conforms in shape to the extremity on which it is adapted to be disposed and a seam formed along the length of the tube in the direction of elongation of the extremity on which it is adapted to be disposed, the seam extending transverse to the lengthwise dimension of the warp-knit power fabric.

It is the primary object of the present invention to provide a relatively inexpensive support garment that has perfect compression gradiations so that the necessary counter pressure is provided along the entire length of the extremity on which the garment is disposed. This and other objects of the invention will become clear from an inspection of the detailed description of the invention and from the appended claims.

BRIEF DESCRIPTION OF THE DRAWINGS

FIG. 1 is a top plan view of a warp-knit power fabric adapted to be cut, having the support garment outline traced thereon;

FIG. 2 is a side view of an exemplary support stocking according to the present invention;

DETAILED DESCRIPTION OF THE DRAWINGS

Figure 3:
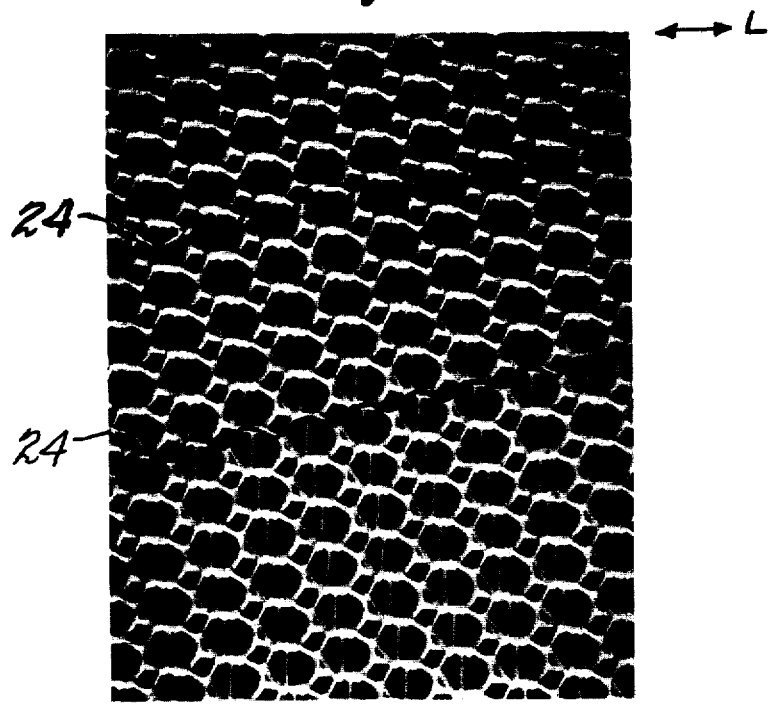
FIG. 3 is a stitch diagram of a closed stitch raschel power fabric which is a suitable fabric for practicing the invention.

The invention will be described with reference to the attached drawings as a support stocking; however, it is to be understood that the invention is equally applicable to support garments for the arms, for other types of support stockings, and for panty hose, leotards, or the like.

FIG. 1 discloses a sheeting of warp-knit power fabric, the fabric having a lengthwise (warp) dimension L (the machine direction and the direction in which spandex threads are laid) of greatest stretch and power, and a filling dimension (the cross-machine direction) in which the stretch is incidental (i.e., about 250%/80% or at least 2/1). A support garment form 12 is cut from the sheet, the sheet being oriented during cutting so that the lengthwise dimension L extends circumferentially in the final garment produced, and the filling dimension F extends longitudinally in the final garment produced (see FIG. 2). The edges of the garment form 12 are seamed as indicated at 14 in FIG. 2, the seam extending along the direction of elongation E of the extremity on which the final support garment 16 is adapted to fit. The cutting step may be practiced while the sheet is disposed as a flat development, as indicated in FIG. 1, or the cutting step may be practiced while the sheet is doubled over. In such a case, conventional sewing machines can be used for cutting and seaming simultaneously. Under some circumstances it is desirable to provide as flat a seam as possible. Such flat seams 14 that are especially suitable can be conventionally made on a Union Special Type No. 503, or a 504, or a Merrow Machine.

The support stocking 16 indicated in FIG. 2 has an open toe 18, but could have other constructions, including closed toes. The stocking 16 is customized in order to provide exactly the right gradient throughout, the leg on which the stocking is to be disposed being measured at intervals to determine the proper dimensions. The cutting step is practiced, based on the results of the measuring step, so that the ankle portions 20 of the stocking 16 provide the maximal compression, and the compression gradually continuously decreases upwardly to the thigh portion 22 of the garment, the compression being minimal at the thigh portion 22. In general, the cutting step is practiced so that the compression provided by the garment is greatest at the portion adapted to be most remote from the torso along the human extremity on which it is adapted to be disposed (i.e., the open toe 18 in the case of a stocking), and the compression gradually accurately and predictably continuously decreases proximally along the extremity toward the torso.

Figure 4:
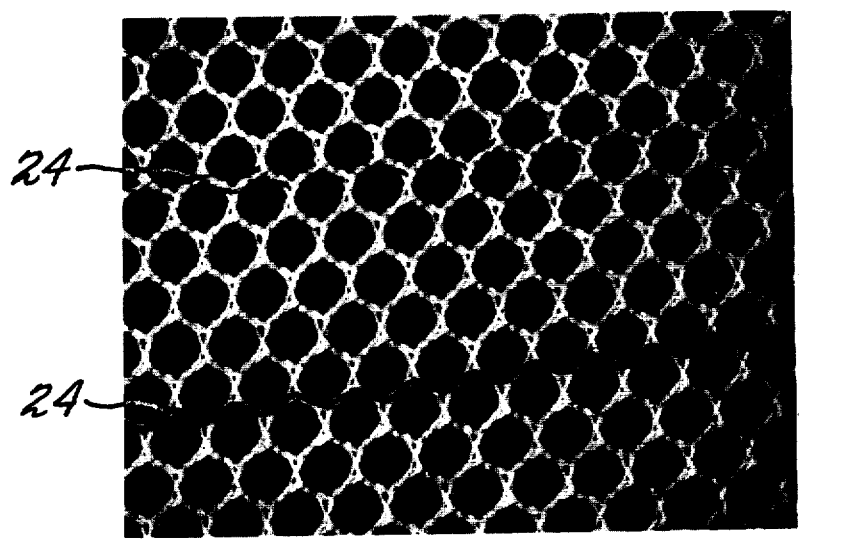
FIG. 4 is a stitch diagram of an open stitch raschel power knit fabric that is suitable for practicing the invention.

Exemplary warp-knit power fabrics that are utilizable in practicing the invention are shown in FIGS. 3 and 4, FIG. 3 being a closed stitch raschel power fabric and FIG. 4 being an open stitch power knit fabric. Tricot and raschel are the preferred warp-knit power fabrics according to the invention. The fabric may have a closed stitch construction having the characteristics of jersey in the relaxed state.

The warp-knit power fabrics have power yarn 24 extending generally in the lengthwise dimension L thereof. The purpose of the power yarn is for imparting measurable compression, as opposed to merely eliminating a tendency to bag or providing a close fit. The power yarn 24 (depicted for clarity of illustration in FIGS. 3 and 4) provides maximum stretch and power in the dimension L, while only incidental fabric stretch is provided in the dimension F perpendicular to L; for instance, the stretch provided in dimension L may be on the order of about 250%, while the stretch provided in dimension F may be on the order of about 80% (a ratio of at least about 2/1). The power yarn may be spandex, rubber, or any other yarn having the distention properties of spandex. The power yarn should have a modulus of elasticity (a measure of force necessary to produce elongation or, conversely, force provided when elongated) that is large enough so that the necessary compression is provided—as opposed to the practically unmeasurable corresponding forces of simple crimped or false twisted yarns which simply relax enough to combat bagging. The accompanying table shows forces necessary to cause (and forces caused by) various % elongations of spandex compared to relaxed crimped or false twisted nylon yarns.

TABLE

YARN FORCE EXERTION
(force given in grams; approximate)
f.t. - false twisted

| % elongation | 20 Denier f.t. nylon | 70 Denier f.t. nylon | 70 Denier Spandex | 140 Denier f.t. nylon | 140 Denier Spandex |
|---|---|---|---|---|---|
| 25 | not measurable | not measurable | 1.1 | .1 | 2 |
| 50 | not measurable | not measurable | 2 | .15 | 3.8 |
| 75 | not measurable | .03 | 3.25 | .25 | 5.8 |
| 100 | .025 | .06 | 4.5 | crimp removed | 7.5 |
| 150 | .1 | .12 | 7.5 | crimp removed | 11.25 |
| 200 | crimp removed | crimp removed | 11 | crimp removed | 15 |
| 250 | crimp | crimp | 15 | crimp | 19 |

TABLE-continued

YARN FORCE EXERTION
(force given in grams; approximate)
f.t. - false twisted

| % elongation | yarn | | | | |
|---|---|---|---|---|---|
| | 20 Denier f.t. nylon | 70 Denier f.t. nylon | 70 Denier Spandex | 140 Denier f.t. nylon | 140 Denier Spandex |
| beyond 250 | removed crimp removed | removed crimp removed | still elongating | removed crimp removed | still elongating |

In evaluating the tabular results above, it should be kept in mind that while 70 and 140 denier false twisted yarn has been tested for the purposes of making a valid comparison, in practice in making stockings having some stretch yarn to minimize bagging (see U.S. Pat. Nos. 2,768,305 and 2,445,049), 20 denier false twisted yarn would probably be used.

The above tabular results indicate that "power" (as that term is used in the present specification and claims) yarn has force exerting and stretching properties many orders of magnitude greater than simple stretch yarn (i.e., 75 times greater force at 100% extension for 70 denier yarn), such characteristics suitable to maintain venous and lymphatic pressures at a given level in an extremity. Seventy denier spandex is emminently suitable for use in the products and methods accoridng to the present invention, although heavier denier yarns can also be used (e.g., 140 denier).

The secondary yarn or yarns 25 which are used in the warp-knit power fabric according to the invention are not critical, any yarn that is capable of being warp-knit being suitable for use as the secondary yarn 25 (i.e., nylon and polyester). The seam 14 always extends transverse to the lengthwise dimension L of the warp-knit power fabric so that circumferential (on the leg) compression is provided by the spandex or like power yarn comprising the power fabric. Due to the great compressive force and stretch in dimension L (the circumferential dimension in the final garment 16 of FIG. 2), yet relatively small stretch in dimension F (the lengthwise dimension in the final garment 16 of FIG. 2), according to the present invention it is possible to make a garment of predictable mechanical compressive properties, the pre-engineered properties not being subject to significant change because of stretching of the fabric in dimension L when placed on the leg of the wearer or because of difficulty of distribution. The final garment according to the invention will not be substantially shorter in the relaxed condition than in the stretched-as-worn condition so that the desired stretch graduations can be maintained at the same relative vertical spacing.

It will thus be seen that according to the present invention it is possible by using simple cut and sew techniques to provide a support garment with the exact counter pressure gradiations necessary in order to be effective to overcome the internal pressure caused by venous-lymphatic abnormalities. The warp-knit power fabric according to the invention provides the necessary compression properties, thus resulting in a support garment that is relatively inexpensive to construct yet has all of the desirable properties of the support garment.

While the invention has been herein shown and described in what is presently conceived to be the most practical preferred embodiment thereof, it will be apparent to those of ordinary skill in the art that many modifications may be made thereof within the scope of the invention, which scope is to be accorded the broadest interpretation of the appended claims so as to encompass all equivalent methods and products.

What is claimed is:

1. A method of manufacturing support garments for elongated extremities comprising the steps of:
    (a) providing a sheet of warp-knit power fabric, the fabric having a lengthwise dimension of greatest stretch and power and a filling dimension in which the stretch is incidental so that desired stretch graduations can be maintained at predetermined longitudinal intervals during use;
    (b) cutting out of the sheet a support garment form, the sheet being oriented during cutting so that the lengthwise dimension of the sheet extends circumferentially in the final garment produced and so that the filling dimension extends longitudinally in the final garment produced; and
    (c) seaming the edges of the garment form to produce the final support garment, the seam extending along the dimension of elongation of the extremity on which the support garment is adapted to fit.

2. A method as recited in claim 1, wherein said cutting step is practiced so that the compression provided by the garment is maximal at the portion thereof adapted to be most remote from the torso along the human extremity on which it is adapted to be disposed, and the compression gradually, accurately and predictably continuously decreases proximally along the extremity toward the torso.

3. A method as recited in claim 1, wherein said cutting step is practiced while said sheet is disposed as a flat development.

4. A method as recited in claim 1, wherein said cutting step is practiced while said sheet is doubled over.

5. A method as recited in claim 4, wherein said cutting and seaming steps are practiced simultaneously.

6. A method as recited in claim 1, wherein said support garment is a support stocking having an open toe, said method comprising the further step of
    measuring the leg on which the stocking is to be disposed, and
    the cutting step being practiced based on the results of said measuring step, so that the ankle portions of the stocking provide maximal compression, and the compression gradually continuously decreases upwardly to the thigh portion of the garment, whereat the compression is minimal.

7. A support garment for an elongated extremity, the garment comprising
    a tube, having a circumference and a length, of warp-knit power fabric conforming in shape to the extremity on which it is adapted to be disposed, the fabric tube having a circumferential dimension of greatest stretch and power and a lengthwise dimension in which the stretch is incidental so that desired stretch graduations can be maintained at predetermined longitudinal intervals during use; and a seam formed along the length of the tube in the direction of elongation of the extremity on which it is adapted to be disposed, the seam extending along the dimension of elongation of the extremity on which the support garment is adapted to fit.

8. A garment as recited in claim 7, wherein the power yarn of the warp-knit power fabric is spandex.

9. A garment as recited in claim 7, wherein said garment is a support stocking having an open toe, and wherein said garment is dimensioned so that the compression provided by said garment is maximal at the ankle portion thereof and continuously decreases gradually up to the thigh portion thereof at which point the compression is minimal.

10. A garment as recited in claim 7, wherein said seam is a flat seam.

11. A garment as recited in claim 7, wherein said warp-knit power fabric is a tricot.

12. A garment as recited in claim 7, wherein said warp-knit power fabric is a raschel.

13. A garment as recited in claim 7, wherein said garment is dimensioned so that the compression provided by said garment is maximal at the portion thereof adapted to be most remote from the torso along the extremity on which it is adapted to be disposed, the compression continuously gradually decreasing proximally along the extremity toward the torso.

14. A garment as recited in claim 7, wherein the power yarn of said warp-knit power fabric exerts a force of approximately 4.5 g at 100% elongation.

15. A garment as recited in claim 7, wherein the fabric stretch in the circumferential dimension is about 250% and the fabric stretch in the lengthwise dimension is about 80%.

16. A garment as recited in claim 7, wherein the fabric stretch in the circumferential dimension is at least about twice as great as the fabric stretch in the lengthwise dimension.

17. A garment as recited in claim 7, wherein the fabric has a closed stitch construction, having the characteristics of jersey in the relaxed state.

* * * * *